US00PP23586P3

(12) United States Plant Patent
Clark et al.

(10) Patent No.: US PP23,586 P3
(45) Date of Patent: May 7, 2013

(54) COLEUS PLANT NAMED 'UF08174'

(50) Latin Name: *Solenostemon scutellarioides*
Varietal Denomination: UF08174

(75) Inventors: David G. Clark, Gainesville, FL (US); Grayson Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 72 days.

(21) Appl. No.: 13/317,128

(22) Filed: Oct. 11, 2011

(65) Prior Publication Data

US 2012/0260377 P1 Oct. 11, 2012

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(57) ABSTRACT

'UF08174' is a new coleus plant distinguished by having stable maroon/lime-green foliage color which maintains bright color in both sun and shade conditions, vigorous mounded habit with excellent branching, and desirable late-flowering characteristics, as disclosed.

2 Drawing Sheets

Genus and species: *Solenostemon scutellarioides.*
Variety denomination: 'UF08174'.

BACKGROUND OF THE INVENTION

The invention relates to a new and distinct variety of coleus plant named 'UF08174'. 'UF08174' originated from open pollination conducted in May-November 2008 in Gainesville, Fla. between the female coleus plant 'UF07312' (unpatented) and an unknown male coleus plant. A single seedling was chosen in May 2008 for further asexual propagation in Gainesville, Fla.

'UF08174' has been reproduced asexually for over three years through vegetative cuttings and has been shown to retain its distinctive characteristics through successive asexual propagations.

Plant Breeder's Rights for this variety have been applied for in Canada on Apr. 6, 2011. 'UF08174' has not been made publicly available more than one year prior to the filing date of this application.

SUMMARY OF THE INVENTION

The following are the most outstanding and distinguishing characteristics of 'UF08174' when grown under normal horticultural practices in Gainesville, Fla.

1. Excellent color for both sunny and shady locations, with a uniform maroon and yellow-green foliage color under high light intensities;
2. Exceptional branching and vigorous growth habit;
3. Good foliage retention until late in the growing season; and
4. Excellent sun and heat tolerance.

DESCRIPTION OF THE PHOTOGRAPHS

This new coleus plant is illustrated by the accompanying photographs which show the plant's form and foliage. The colors shown are as true as can be reasonably obtained by conventional photographic procedures. The photographs were taken from 3-month-old plants grown from cuttings in 5 inch pots and transplanted to display/trial gardens during June-August 2011 in Citra, Fla. and Gainesville, Fla.

DESCRIPTION OF THE NEW VARIETY

Figure 1:
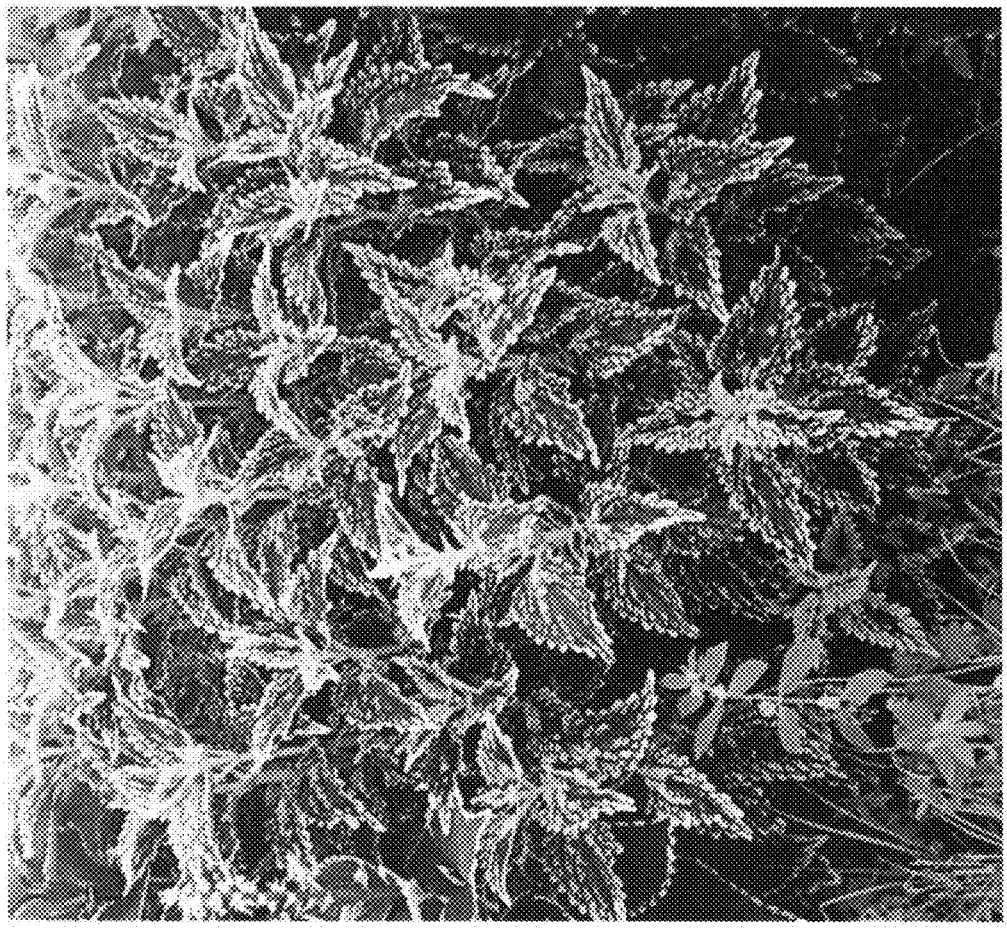
FIG. 1 shows the growth habit, form, and foliage of the instant plant.
Figure 2:
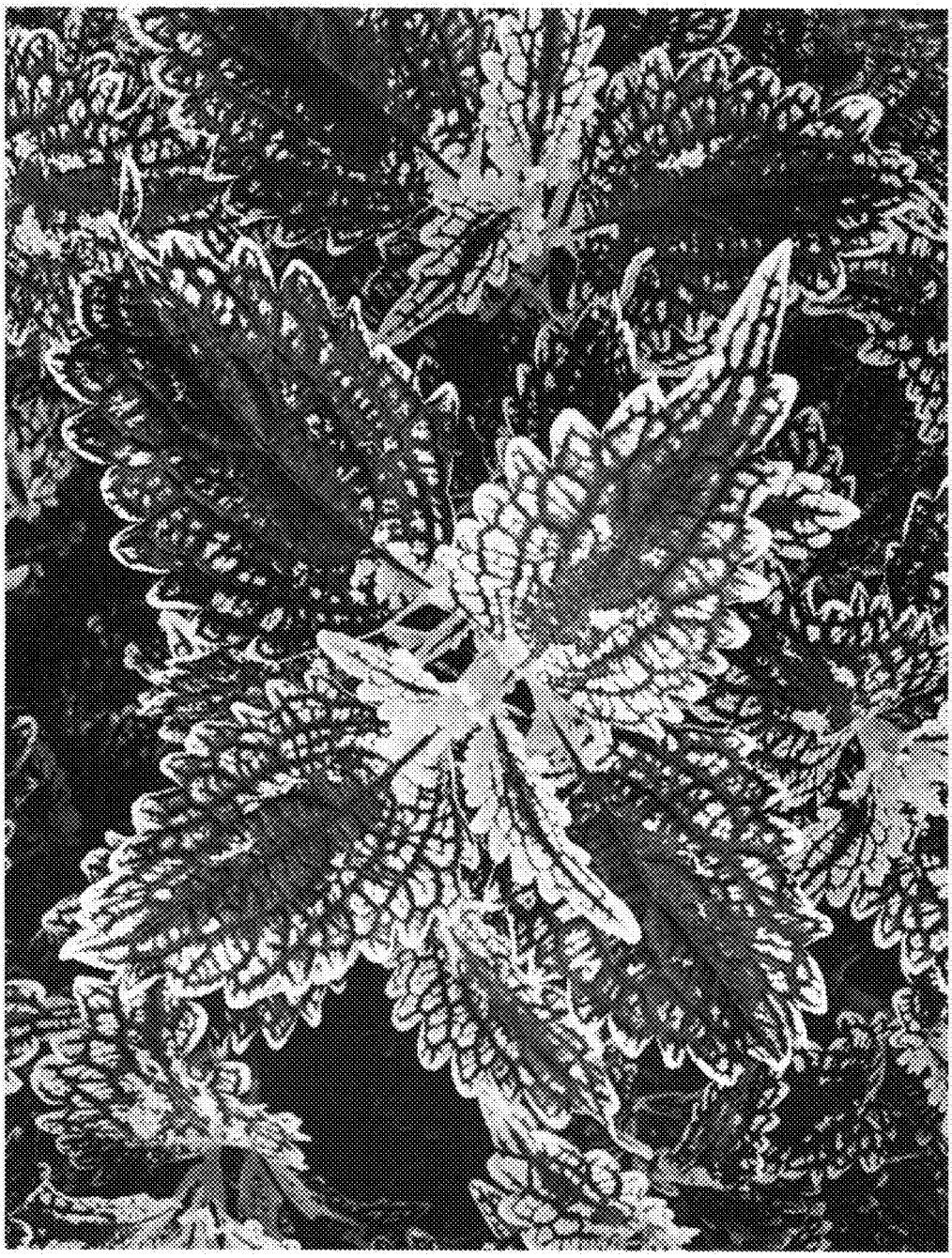
FIG. 2 shows a close-up of the foliage.

The following detailed description sets forth the distinctive characteristics of 'UF08174'. The detailed description was taken on 2-month-old plants from cuttings, growing in a glass greenhouse in Gainesville, Fla. in early spring 2011. The plants were pinched 2 weeks after cuttings were rooted, then grown in 1 gallon pots for approximately 10 weeks. Color references are to The R.H.S Colour Chart of The Royal Horticultural Society of London (R.H.S.), 2001 Edition.

DETAILED BOTANICAL DESCRIPTION

Classification:
- *Family.*—Lamiaceae.
- *Botanical.*—*Solenostemon scutellarioides.*
- *Common name.*—Coleus.
- *Variety name.*—'UF08174'.

Plant description:
- *Form.*—Mounded.
- *Habit.*—Upright.
- *Height* (*from top of soil*).—35 cm.
- *Width* (*horizontal plant diameter*).—40 cm.

Propagation:
- *Type cuttings.*—Vegetative meristems having at least 1 node.
- *Time to initiate roots.*—3-4 days.
- *Time to produce a rooted cutting.*—7-10 days.
- *Root habit.*—Fibrous.
- *Root description.*—Callus forms in 2 to 3 days, roots initiate in 3-4 days and become a highly branched cutting in 7-10 days.

Branches:

*Quantity per plant.*—20 to 30 per plant, pinched once.

*Branch color.*—RHS 144A (yellow-green); nodes are banded RHS 183C (grayed-purple).

*Texture.*—Smooth.

*Pubescence.*—Non-descript.

*Stem description.*—Square shaped stem, 1.4 cm in diameter at the soil line.

*Branch diameter.*—0.6 cm at the base of a 11 cm long branch.

*Branch length.*—11 cm.

*Internode length.*—1.5-5 cm.

*Anthocyanin.*—N/A.

Leaves:

*Quantity of leaves per branch.*—10 to 12.

*Arrangement.*—Opposite.

*Fragrance.*—Not fragrant.

*Shape.*—Undulated, lobed.

*Length.*—11-12 cm.

*Width.*—6-7 cm.

*Apex.*—Caudate.

*Base.*—Attenuate.

*Margin.*—Lobed.

*Leaf texture* (*both surfaces*).—Slightly pubescent; velvet-like upper surface.

*Pubescence color* (*both surfaces*).—Non-descript with naked eye.

*Venation color.*—Upper surface: RHS 187A (greyed-purple). Lower surface: RHS 187C (greyed-purple).

*Color, mature and immature leaf.*—Upper surface: primarily RHS 59B (red-purple), with interveinal areas and margins colored RHS 144A (yellow-green); leaf veins are colored RHS 187A (grey-purple) transitioning. Lower surface: RHS 59B (red-purple) masked with RHS 146C (yellow-green), with leaf veins colored RHS 187C (greyed-purple).

*Petiole length.*—3 cm to 4 cm.

*Petiole diameter.*—0.4-0.5 cm.

*Petiole color.*—RHS 144A (yellow-green).

Flowers, fruit and seeds: Flowers, fruit and seeds have not been observed.

Disease and insect resistance: Disease and insect resistance is typical of the species.

COMPARISON WITH PARENTAL LINES AND KNOWN VARIETY

When 'UF08174' is compared to the female parent 'UF07312' (unpatented), 'UF08174' has maroon lance-shaped foliage mottled with bright green around the leaf margins, while 'UF07312' had leaves colored maroon with pink and green veins and mottling with leaf serrated margin.

When 'UF08174' is compared to the commercial variety 'UF084624' (unpatented), plants of 'UF084624' have bright red foliage mottled with bright green around the leaf margins that is irregularly and loosely lobed around the leaf edge; whereas 'UF08174' has maroon lance-shaped foliage mottled with bright green around the leaf margins and has more lateral branches than 'UF084624'. 'UF08174' and commercial variety 'UF084624' (unpatented) plants both have loosely mounded habit, but 'UF08174' is more vigorous and has larger leaves than 'UF084624'.

We claim:

1. A new and distinct variety of coleus plant as shown and described herein.

* * * * *